United States Patent
Matsumura et al.

(10) Patent No.: US 7,177,673 B2
(45) Date of Patent: Feb. 13, 2007

(54) MEDICAL TELEMETRY SYSTEM

(75) Inventors: Fumiyuki Matsumura, Tokyo (JP); Iwao Takahashi, Tokyo (JP); Tadashi Nakayama, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 484 days.

(21) Appl. No.: 10/122,724

(22) Filed: Apr. 16, 2002

(65) Prior Publication Data

US 2002/0161308 A1 Oct. 31, 2002

(30) Foreign Application Priority Data

Apr. 16, 2001 (JP) .................... P2001-116717

(51) Int. Cl.
*A61B 5/0428* (2006.01)
*A61B 5/0432* (2006.01)

(52) U.S. Cl. .................. 600/523; 439/909; 607/60

(58) Field of Classification Search ........... 128/903; 600/372, 382, 386, 394, 508–509, 513, 522–523, 600/525; 607/30–32, 59, 60, 115, 149, 152, 607/148, 142

See application file for complete search history.

(56) References Cited

U.S. PATENT DOCUMENTS

| | | | | |
|---|---|---|---|---|
| 4,506,678 A | * | 3/1985 | Russell et al. | 600/536 |
| 5,307,818 A | * | 5/1994 | Segalowitz | 600/509 |
| 5,343,869 A | * | 9/1994 | Pross et al. | 600/301 |
| 5,666,958 A | * | 9/1997 | Rothenberg et al. | 600/509 |
| 5,694,940 A | * | 12/1997 | Unger et al. | 600/509 |
| 6,267,723 B1 | * | 7/2001 | Matsumura et al. | 600/300 |
| 6,856,832 B1 | * | 2/2005 | Matsumura et al. | 600/523 |

* cited by examiner

*Primary Examiner*—Robert E. Pezzuto
*Assistant Examiner*—Kristen Mullen
(74) *Attorney, Agent, or Firm*—Sughrue Mion, PLLC

(57) ABSTRACT

A medical telemetry system includes a first detection section for detecting a first vital sign signal using a first sensor, a transmitter 10 which modulates a signal detected by the first detection section and transmits the modulated signal by radio wave transmission, a receiver 30 which receives the detection signal that has been transmitted by radio wave transmission and demodulates the received signal, having a connector 32 for transmitting the demodulated signal to a vital sign signal input section of the vital sign signal monitor 20, wherein the connector 32 of the receiver is connectable with a commonly used vital sign signal input section of each of various types of vital sign signal monitors 20.

16 Claims, 12 Drawing Sheets

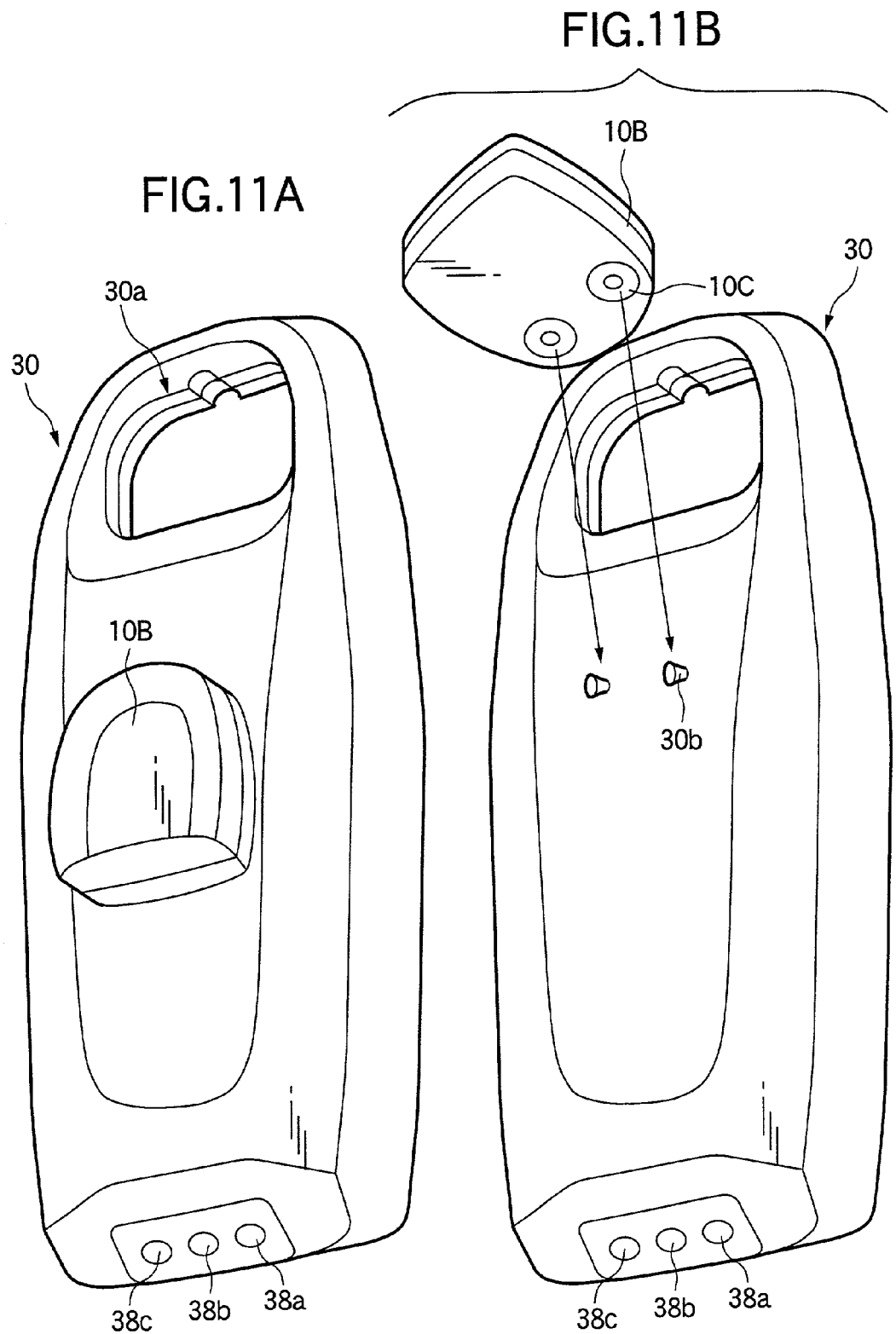

MEDICAL TELEMETRY SYSTEM

BACKGROUND OF THE INVENTION

1. Field of invention

The present invention relates to a medical telemetry system which collects signals representing various vital signs measured by a vital sign signal measurement device or the like in order to obtain vital sign information about a patient and which, by wireless communication, can remotely transmit the thus-collected vital sign information to a vital sign signal monitor connected to a host computer or the like. Particularly, the present invention relates to a medical telemetry system which takes a vital sign signal monitor configured to collect a vital sign signal by wire communication as a vital sign signal monitor configured to collect a vital sign signal by wireless communication with easy, simple, and compatible connection.

2. Related Art

There have already been put into practice a wire system vital sign signal monitor which is configured to send, using a relay cord or the like to a vital sign signal monitor, a vital sign signal corresponding to any one or a combination of measured analog vital sign signals, such as an electrocardiographic signal, a pulse wave signal, and a respiratory activity signal, all being obtained directly from a sensor such as an electrode attached to a living body; and a wireless vital sign signal monitor which modulates the vital sign signal as required and transmits the thus-modulated signal to a vital sign signal monitor by a wireless transmitter.

SUMMARY OF THE INVENTION

The object of the invention is to provide a medical telemetry system constructed so as to enable easy, simple use of a vital sign signal monitor of either a wireless system or a wire system, by providing the vital sign signal monitor with a transmitter for detecting a vital sign signal and transmitting the thus-detected signal by radio wave transmission; a connector capable of being detachably connected to the vital sign signal monitor by a relay cord; and a receiver for receiving a vital sign signal from the transmitter.

To achieve the object, there is provided a medical telemetry system comprising:

a transmitter having a first detection section for detecting a first vital sign signal from a first sensor and a modulation circuit for modulating a signal detected by the first detection section to transmit the modulated signal by radio wave transmission;

a receiver having demodulation means for receiving the detection signal transmitted by radio wave transmission and for demodulating the received signal and a connector for transmitting the demodulated signal output by the demodulation means to a vital sign signal input section of the vital sign signal monitor, wherein the connector of the receiver is connectable with a commonly used vital sign signal input section of each of various types of vital sign signal monitors.

In this case, the connector is provided on an adapter which can be detachably attached to the receiver.

Preferably, the medical telemetry system further comprises a second detection section for detecting a second vital sign signal using the first sensor.

Further, the transmitter can be provided with a control section for multiplexing a signal detected by the first detection section and a signal detected by the second detection section and transmit a multiplexed signal output from the control section.

Preferably, the medical telemetry system further comprises a second detection section for detecting a second vital sign signal using other than the first sensor.

A transmitter can be provided with a control section for multiplexing a signal detected by the first detection section and a signal detected by the second detection section and transmits a multiplexed signal output from the control section.

Preferably, the receiver comprises a control section for receiving the multiplexed signal that has been transmitted from the transmitter and separating the received signal, and superimposing means for superimposing the first vital sign signal and the second vital sign signal can be provided on a signal line from the control section to the connector.

Preferably, the receiver further comprises:

second detection means for detecting the second vital sign signal; and superimposing means for superimposing the second vital sign signal detected by the second detection section and the first vital sign signal, wherein the second detection means and the superimposing means are provided on a signal line for transmitting the first vital sign signal to the connector.

Preferably, the medical telemetry system further comprises:

a sensor detachment detection section for detecting detachment of the first sensor;

wherein the transmitter is provided with a control section for multiplexing a signal detected by the first detection section and a signal output from the sensor detachment detection section and transmits a multiplexed signal output from the control section; and the receiver is provided with a control section for receiving the multiplexed signal and separating the received signal; a switch provided on a signal line from the control section to the connector; and a switch control section for performing a control operation so as to turn off the switch in order to reproduce detachment of the sensor when the sensor has been detached, in accordance with a signal from among the separated signals, output from the sensor detachment detection section.

Preferably, the first sensor has a plurality of electrodes for detecting an electrocardiographic waveform; the sensor detachment detection section detects detachment of any of the plurality of electrodes; and the receiver is provided with switches provided on signal lines from the control section to terminals of the connector and are assigned to the plurality of electrodes, wherein the switch control section performs a control operation for turning off a switch of a signal line extending to the terminal corresponding to an electrode which is determined as having been detached by the sensor detachment detection section.

Preferably, the first sensor comprises an electrocardiographic waveform detection electrode having a terminal, which terminals is to be connected with a commonly used hook or clip for use with an electrocardiographic waveform detection electrode and intended for leading an electric potential of the heart;

the first detection section comprises an electrocardiographic waveform detection section for detecting an electrocardiographic waveform as a first vital sign signal;

the commonly used vital sign signal input section has the commonly used hook or clip for use with an electrocardiographic waveform detection electrode; and the connector has a terminal which is connectable by the commonly used hook or clip.

Preferably, the superimposing means superimposes a second vital sign signal detected by the second detection section or the second detection means on a signal line which transmits the first vital sign signal and extends to the connector, in the form of impedance changes.

Preferably, the second detection section or the second detection means can be constituted of a respiratory status detector which detects respiratory action as a second vital sign signal.

Further, there is provided an electric circuit for reproducing detachment of a sensor for detecting a vital sign signal, comprising:

a signal line for transmitting a vital sign signal;
a switch which is provided on the signal line for reproducing detachment of the sensor by deactivation; and
a switch control section for deactivating the switch on the basis of detection of sensor detachment.

The switch has a characteristic of leakage current flowing from the switch being lower than a predetermined current value when the power for activating the switch supplied from the power supply section has become consumed.

By this characteristic, when the receiver cannot demodulate received signals due to lack of supplied power, the receiver can prevent the vital sign signal monitor from erroneously recognizing that the low leakage current from switch is signal detected by the sensor. At that time, the leakage current is lower than the predetermined current value, so the vital sign signal monitor recognizes that the switch is turned off.

Moreover, the predetermined current value can be a current threshold value at which the vital sign signal monitor recognizes detachment of a sensor. As a result, when the receiver cannot demodulate received signals due to lack of supplied power, the receiver can prevent the vital sign signal monitor from erroneously recognizing that the low leakage current from switch is signal detected by the sensor. At that time, the leakage current is lower than the current threshold value for recognizing detachment of a sensor, so the vital sign signal monitor recognizes that the switch is turned off.

More preferably, the switch becomes completely deactivated when the power supplied from the power supply section has become consumed.

Further, preferably, a photo-MOS relay is employed as the switch having such a characteristic.

BRIEF DESCRIPTION OF DRAWINGS

FIGS. 11A and 11B are perspective views of combination of the wireless receiver and the wireless transmitter.

DETAILED DESCRIPTION OF PRFEREED EMBODIMENTS

An embodiment of a medical telemetry system according to the invention will be described hereinbelow in detail by reference to the accompanying drawings.

Figure 1:
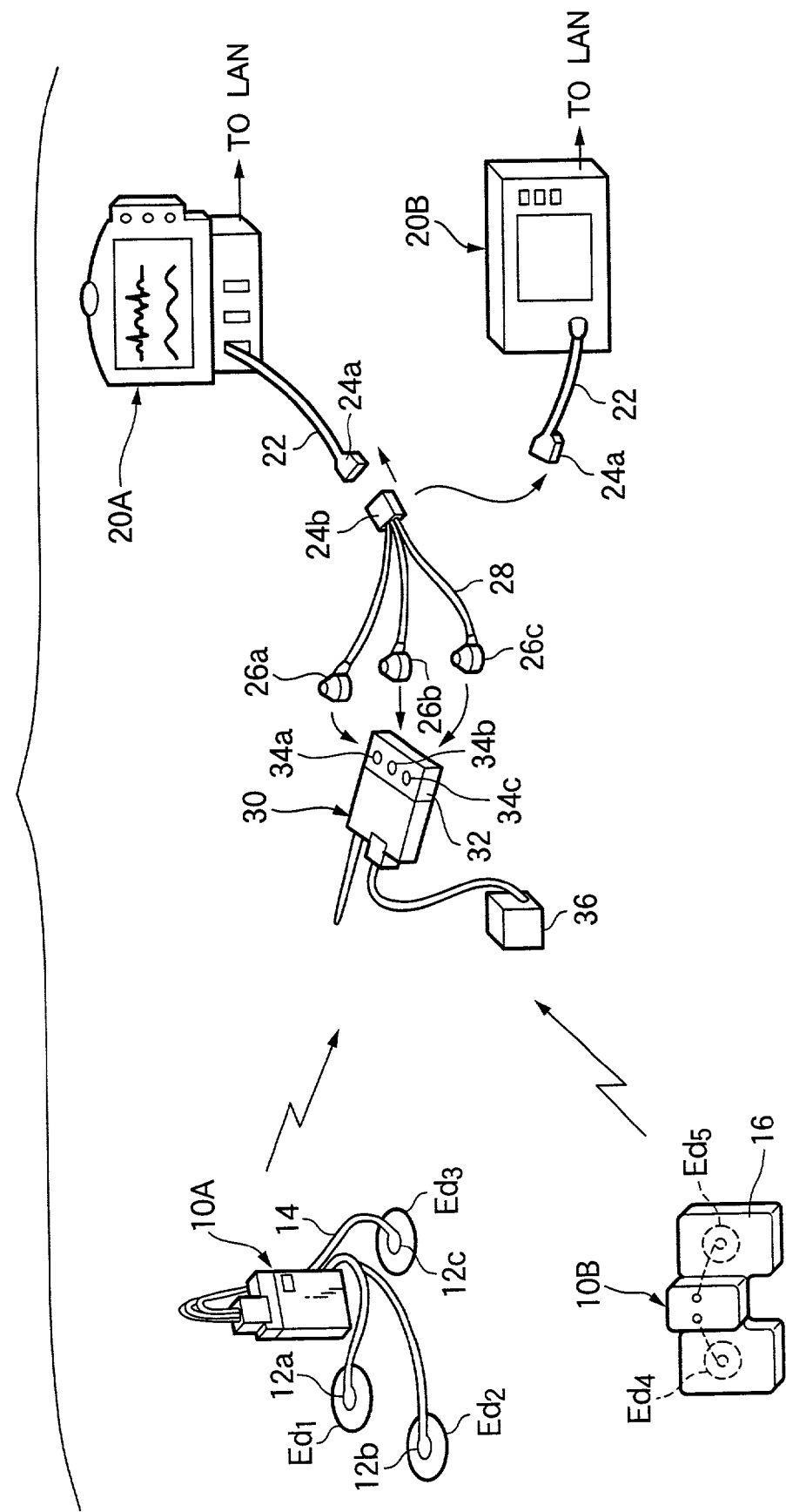
FIG. 1 is a schematic system block diagram showing an embodiment of a medical telemetry system according to the invention.

FIG. 1 is a descriptive view for schematically showing the configuration of a medical telemetry system according to the invention. As shown in FIG. 1, reference numeral 10A denotes an embodiment of a transmitter for sending a vital sign signal by radio wave transmission. The transmitter 10A is connected to three lead electrodes Ed1, Ed2, and Ed3 to be attached to, e.g., tissue surface or body surface (i.e., the skin), by corresponding connection cords 14. The connection cords 14 have connecting terminals 12a, 12b, and 12c for electrode hooks or clips etc. Reference numeral 10B designates another embodiment of a transmitter which sends a vital sign signal by radio wave transmission. The transmitter 10B is detachably connected to, e.g., two adhesive pads 16 which have two lead electrodes Ed4, Ed5 and are to be attached directly to tissue surface.

Reference numerals 20A, 20B designate vital sign signal monitors of different types. A relay cord 22 extends from each of the vital sign signal monitors 20A, 20B. A coupler 24a to be used for connection with another cord is provided at the extremity of each relay cord 22. The relay cord 22 is to be connected to a connection cord 28. Provided at one end of the connection cord 28 are connecting terminals 26a, 26b, and 26c for electrode hooks or clips etc. which can be connected directly to lead electrodes (e.g., Ed1, Ed2, and Ed3). Provided at the other end of the connection cord 28 is a coupler 24b capable of being connected to the coupler 24a of either one of the relay cords 22.

The transmitter 10 (i.e., the transmitters 10A and 10B; the same convention also applies to corresponding descriptions) is constituted as a transmitter to be applied to a related art wireless vital sign signal monitor. The vital sign signal monitor 20 (i.e., the monitors 20A and 20B; the same convention also applies to corresponding descriptions) is constituted as a related art wire vital sign signal monitor. The medical telemetry system according to the embodiment is provided with a wireless receiver 30 having a connector 32 serving as means for coupling the transmitter 10 with the vital sign signal monitor 20 by wireless transmission.

A connector 32 is provided integrally in the receiver 30 according to the embodiment. The connector 32 has terminals 34*a*, 34*b*, and 34*c* which are detachably connected to the connecting terminals 26*a*, 26*b*, and 26*c* for electrode hooks or clips etc., provided at one end of the connection cord 28 to be connected to the relay cord 22 of the vital sign signal monitor 20. Vital sign signal detection means 36 may be connected to a part of the receiver 30 for entering a second vital sign signal different from the first vital sign signal transmitted from the transmitter 10. Details of the vital sign signal detection means 36 to be used for entering the second vital sign signal will be described later.

As mentioned previously, in the embodiment, the medical telemetry system is provided with the wireless receiver 30 having the connector 32. As a result, various related art vital sign signal monitors 20 and various wireless transmitters 10 that have been known in the art are each coupled together in a compatible manner, enabling effective use of the medical telemetry system.

Figure 2:
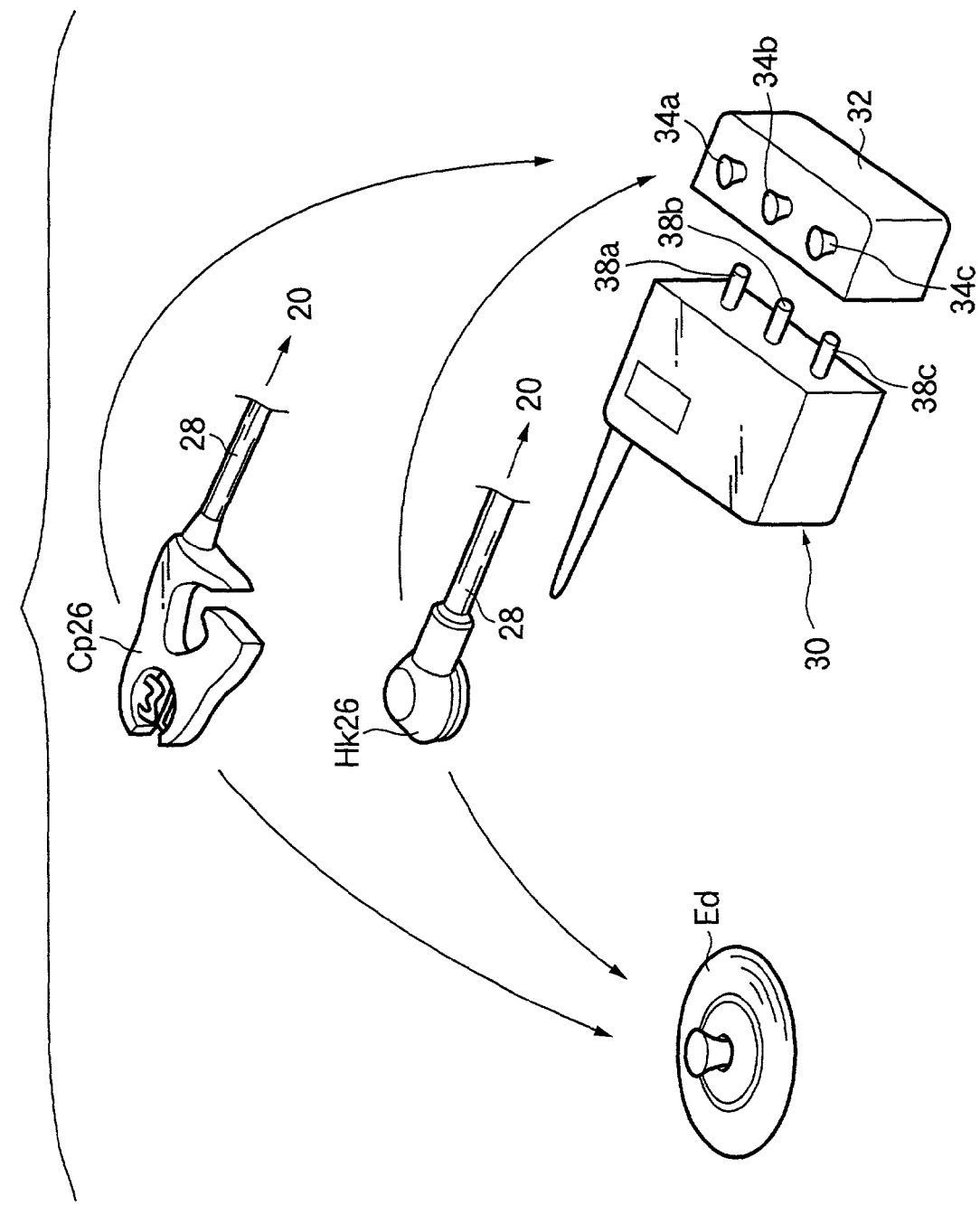
FIG. 2 is a descriptive view showing the configuration of a wireless receiver used in the medical telemetry system according to the invention.

FIG. 2 is a descriptive view showing the connection of the aforementioned wireless receiver 30. The connector 32 is configured as a detachable adapter which is detachable to the main body by coupling terminals 38*a*, 38*b*, and 38*c* provided in part of the receiver main body. Terminals 34*a*, 34*b*, and 34*c* provided on the connector 32 can be simply and reliably attached to electrode hooks Hk26 or clips Cp26 provided at one end of the connection cord 28 connected to the vital sign signal monitor 20. Here, reference numeral Ed designates a lead electrode having a connecting terminal to be attached to tissue surface.

Example circuit configurations of the wireless transmitter 10 of the medical telemetry system according to the invention and those of the wireless receiver 30 of the same will be described by reference to the accompanying drawings.

Configuration First Example of the Wireless Transmitter 10

Figure 3:
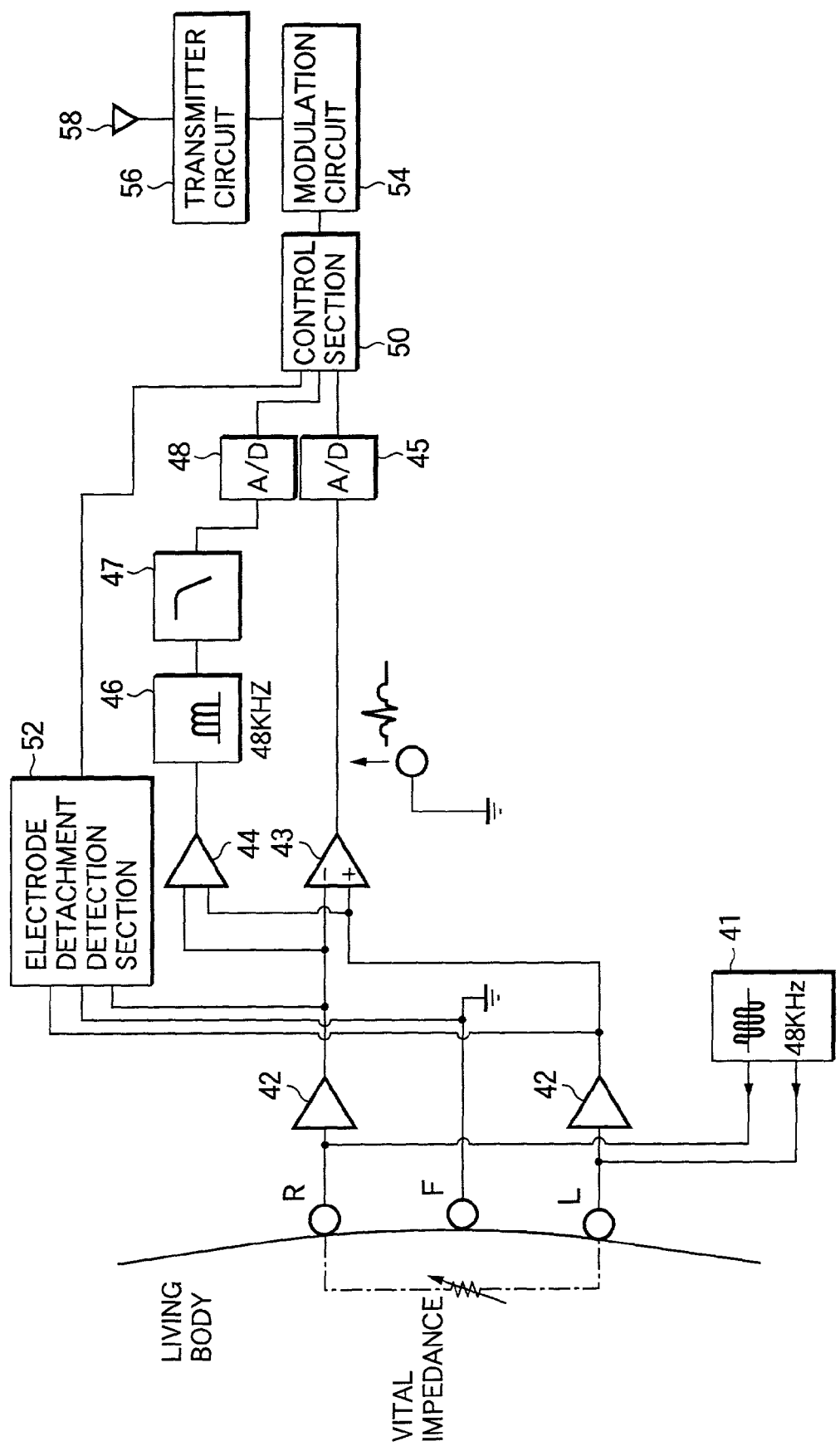
FIG. 3 is a block diagram showing a circuit configuration example of a wireless transmitter used in the medical telemetry system according to the invention.

FIG. 3 shows an embodiment of a circuit configuration of the wireless transmitter 10 constituting the medical telemetry system of the invention. In the embodiment, there are provided three electrodes R, F, and L for detecting vital sign signals (the electrode F is to be grounded). The electrodes R, L detect a synthesized signal constituted of an electrocardiographic waveform signal and a vital sign impedance waveform signal stemming from respiratory action. Thus synthesized vital sign signals are synthesized with a 48-kHz signal supplied from a constant current source 41. The vital sign signals flow through amplifiers 42, 43, whereby an electrocardiographic waveform signal is obtained. The thus-obtained waveform signal is input to a control section 50 through an A/D converter 45. The vital sign signal synthesized with the 48-kHz signal supplied from the constant current source 41 flows through the amplifiers 42, an amplifier 44, a detector/half-wave rectifier 46, and a high pass filter 47, whereby a vital sign impedance waveform signal is produced. The thus-produced waveform signal is input to the control section 50 through the A/D converter 48. An electrode-detached status detected by the electrodes R, F, and L is detected by an electrode detachment detection section 52. The resultant electrode detachment detection signal is input to the control section 50.

In this way, separated signals which have been input to the control section 50 and consist of the electrocardiographic waveform signal, the vital sign impedance waveform signal, and the electrode detachment detection signal are multiplexed. The thus-multiplexed signal is sent to the wireless receiver 30 through a modulation circuit 54, a transmitter circuit 56, and an antenna 58. In the embodiment, the electrodes R, F, and L correspond to the connecting terminals 12*a*, 12*b*, and 12*c* for electrode hooks or clips etc. to be connected to the lead electrodes Ed1, Ed2, and Ed3 of the transmitter 10A shown in FIG. 1.

Configuration Second Example of the Wireless Transmitter 10

Figure 4:
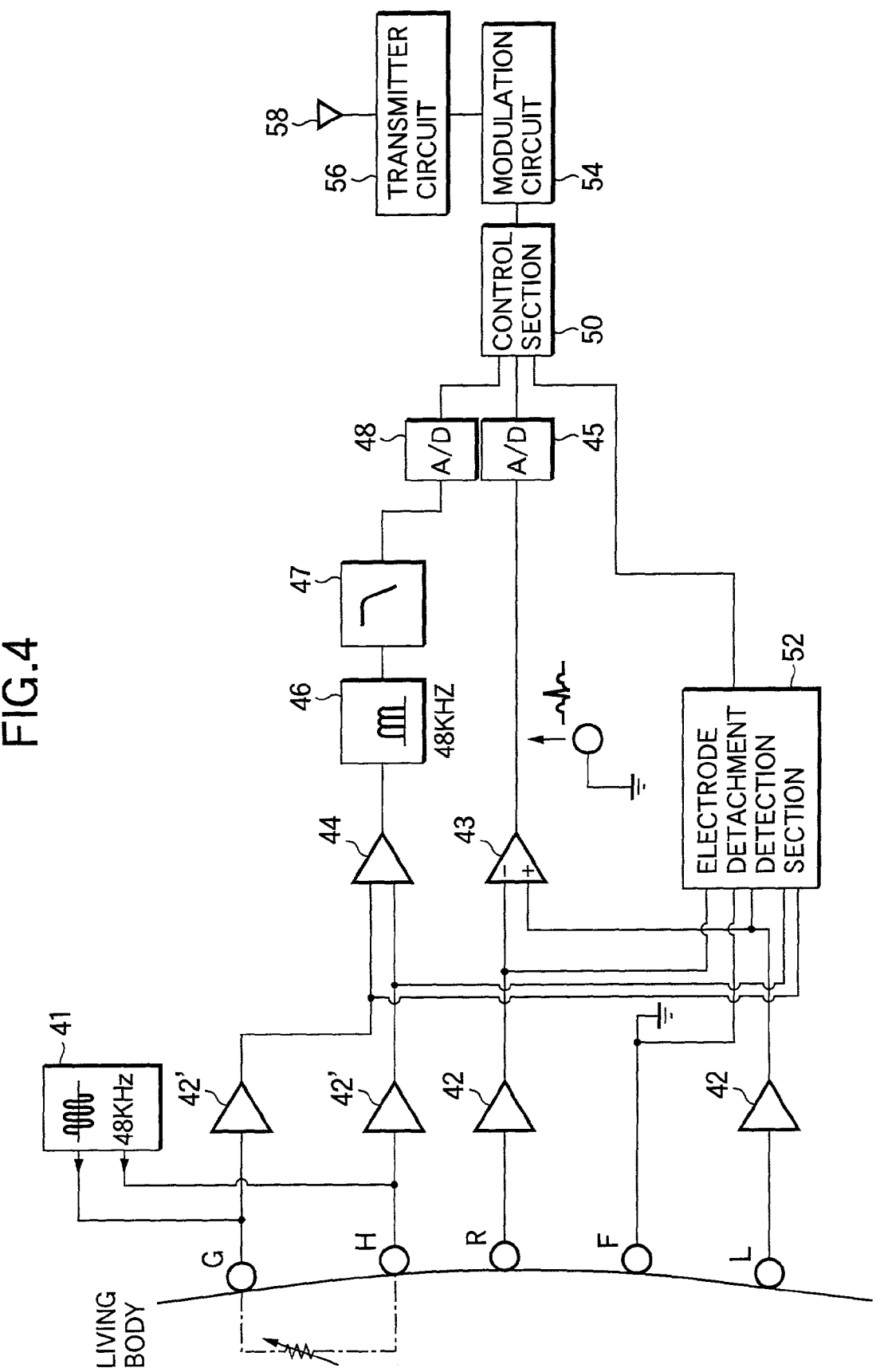
FIG. 4 is a block diagram showing another circuit configuration example of the wireless transmitter used in the medical telemetry system according to the invention.

FIG. 4 shows another embodiment of a circuit configuration of the wireless transmitter 10 constituting the medical telemetry system of the invention. In this embodiment, the electrocardiographic waveform signal is detected by one electrode, and the vital sign impedance waveform signal stemming from respiratory action is detected by another electrode. More specifically, the electrocardiographic waveform signal is detected by the three electrodes R, F, and L in the same manner as in the previous embodiment, and the thus-detected signals are input to the control section 50. In this case, the electrode detachment detection signal is also detected in the same manner as in the previous embodiment, and the thus-detected signal is sent to the control section 50. Like constituent elements are assigned like reference numerals, and their explanations are omitted. The vital sign impedance waveform signal is detected by electrodes G, H, and the signal is synthesized with the 48-kHz signal supplied from the constant current source 41. The thus-synthesized signal is input to the control section 50 through amplifiers 42', 44, the detector/half-wave rectifier 46, the high pass filter 47, and an A/D converter 48.

In this way, the electrocardiographic waveform signal, the vital sign impedance waveform signal, and the electrode detachment detection signal, which have been input to the control section 50, are multiplexed and transmitted as a multiplexed signal to the wireless receiver 30 in the same manner as in the previous embodiment.

Configuration First Example of the Wireless Receiver 30

Figure 5A:
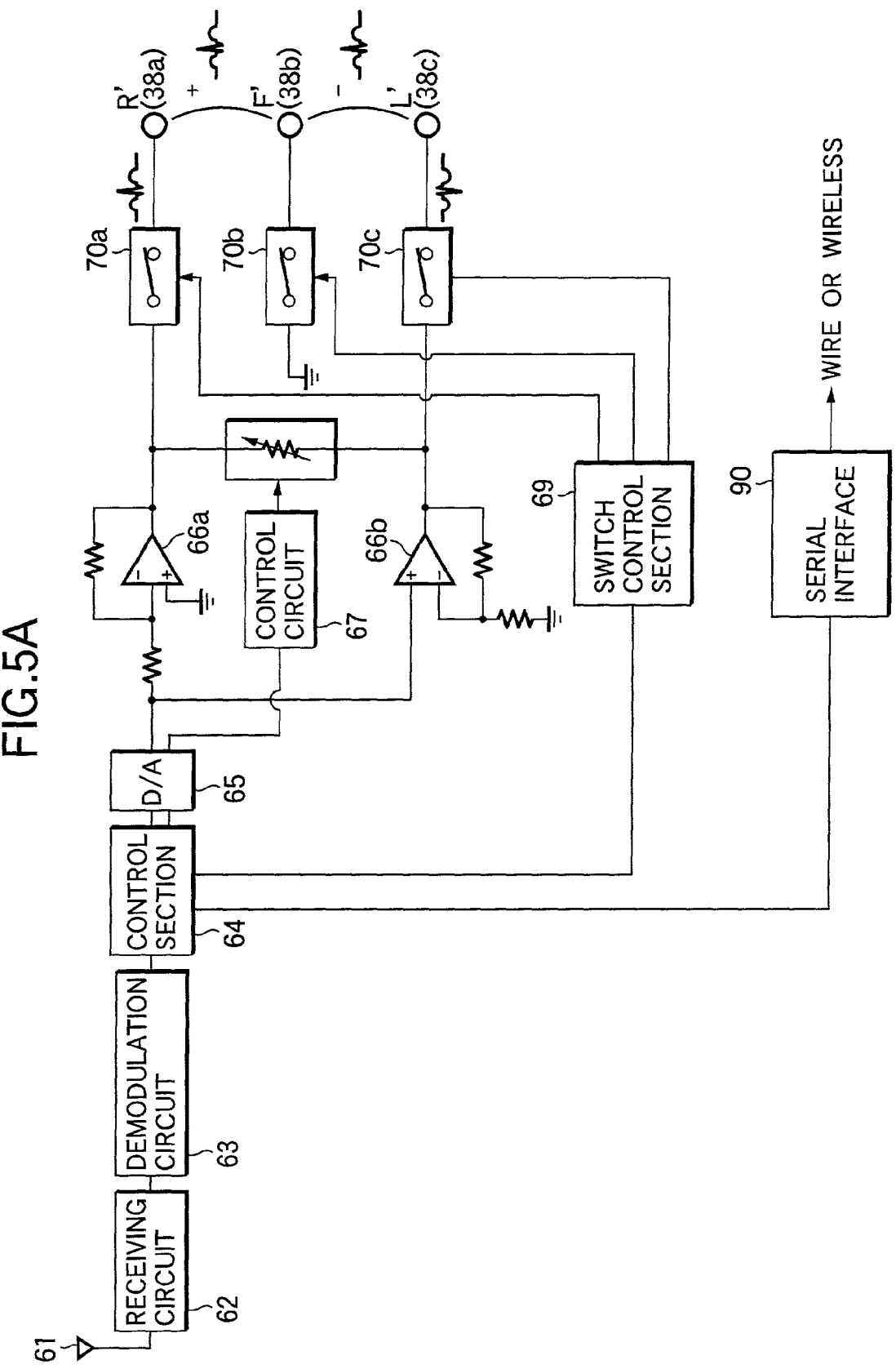
FIG. 5A is a block diagram showing a circuit configuration example of a wireless receiver used in the medical telemetry system according to the invention.
Figure 5B:
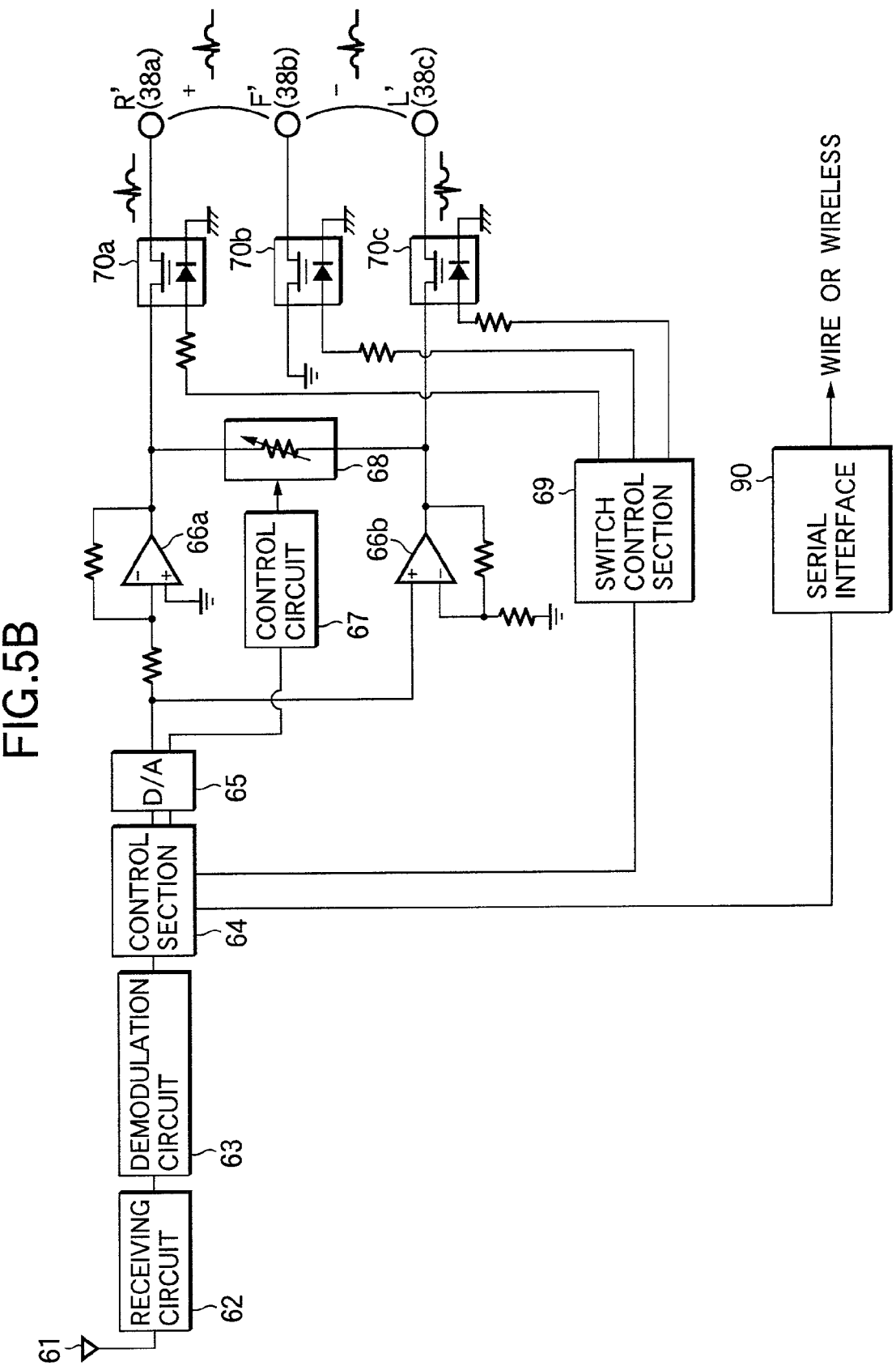
FIG. 5B is a block diagram showing a circuit configuration example of a wireless receiver used in the medical telemetry system according to the invention.

FIGS. 5A and 5B show embodiments of circuit configurations of a wireless receiver 30 constituting the medical telemetry system of the invention. In the embodiment, the receiver 30 is configured to receive and demodulate the multiplexed signal which has been sent by the wireless transmitter 10 shown in FIGS. 4 and 5A and consists of the electrocardiographic waveform signal, the vital sign impedance waveform signal, and the electrode detachment detection signal. The thus-demodulated signals are transmitted to the vital sign signal monitor 20. In the wireless receiver 30 of the present embodiment, the signal received by an antenna 61 is input to a control section 64 through a receiving circuit 62 and a demodulation circuit 63. The multiplexed signal input to the control section 50 is separated into the electrocardiographic waveform signal, the vital sign impedance waveform signal, and the electrode detachment detection signal. The electrocardiographic waveform signal and the vital sign impedance waveform signal are received as the multiplexed signal, the vital sign signal detection means 36 shown in FIG. 1 is unnecessary.

The electrocardiographic waveform signal input to the control section 50 can be output at output terminals R', F', and L' through a D/A converter 65 and differential amplifiers 66*a*, 66*b*. The vital sign impedance waveform signal can be reproduced while being superimposed on the electrocardiographic waveform signal through the D/A converter 65 and the control circuit 67, by a pseudo resistor serving as superimposing means 68 connected between the output terminal R' of the differential amplifier 66*a* and the output terminal L' of the differential amplifier 66*b*. In connection with the electrode detachment detection signal, signals corresponding to the respective electrodes can be output from the control section 64 by a switch control section 69. The electrode detachment detection signals perform control operations so as to activate (on)/deactivate (off) switches 70a, 70b, and 70c provided on signal lines assigned to the output terminals R', F', and L'. In the embodiment, the output terminals R', F', and L' correspond to the coupling terminals 38a, 38b, and 38c described in connection with the embodiment shown in FIG. 2.

A serial interface 90 can send an electrocardiographic waveform signal and a vital sign impedance signal to a general personal computer by wire or wireless transmitter. An IrDA, an RS-232C, an USB port, and a bi-directional wireless interface can be applied to the serial interface.

As shown in FIG. 5B, there will now be shown an example in which photo-MOS relays are employed for the switches 70a, 70b, and 70c.

Power is supplied from a power supply section (e.g., a battery cell) for activating the respective photo-MOS relays and a signal is output from the switch control section 69 to control activating/deactivating the respective photo-MOS relays.

The reason for adopting photo-MOS relays is that the respective photo-MOS relays can be completely deactivated when a battery cell used for driving the receiver has become completely consumed.

If the receiver is turned on because of the characteristics of a switch while the battery cell has become completely consumed and all functions of the receiver have become inoperative (e.g., a state in which the receiver cannot demodulate an electrocardiographic waveform signal or the like), a vital sign signal monitor connected to the receiver recognizes that there is no vital sign signal and displays a base line. As a result, there is issued an alarm warning of asystole.

In order to prevent occurrence of such an alarm, when the battery cell has become consumed and the functions of the receiver have become inoperative, the photo-MOS relays are turned off completely. As a result, the vital sign signal monitor connected to the receiver can display detachment of electrodes, thus preventing occurrence of erroneous diagnosis.

Complete deactivation of the photo-MOS relays implies the following technical significance. In order to detect detachment of electrodes, the vital sign signal monitor usually causes very weak current to flow through electrodes by lead wires. When the electric current flowing into the lead wires from another electrode is under a predetermined, very weak current value (e.g., 10 nA), the monitor determines that the electrode has become detached. At least when a battery cell has become consumed, leakage current, which flows to a switch, must be under the predetermined current value. If switches have such a characteristic, the vital sign signal monitor can determine that the switches have been completely turned off at the time of battery drain. As a matter of course, desired switches involve occurrence of no leakage current and enable complete deactivation.

The switches are not limited to photo-MOS relays and may be embodied by other switches, so long as the switches are completely deactivated when power supply has become insufficient at the time of battery drain (i.e., when the functions of the receiver have become stopped).

Configuration Second Example of the Wireless Receiver 30

Figure 6:
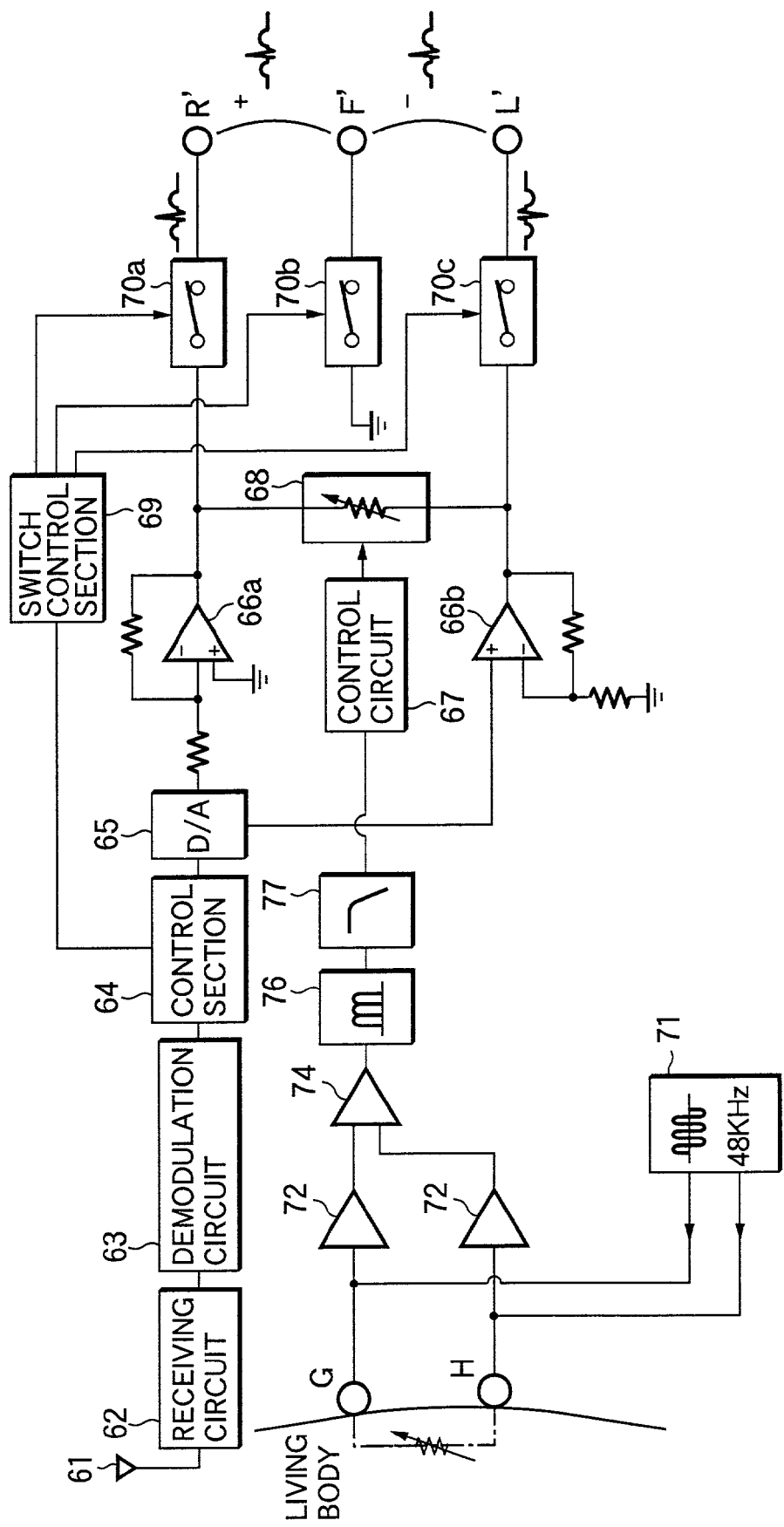
FIG. 6 is a block diagram showing another circuit configuration example of the wireless receiver used in the medical telemetry system according to the invention.

FIG. 6 shows another embodiment of circuit configuration of a wireless receiver 30 constituting the medical telemetry system of the invention. In the embodiment, the wireless transmitter 10 transmits only an electrocardiographic waveform signal and an electrode detachment detection signal. The system is constructed such that second vital sign signal detection means 36 (shown in FIG. 1) provided in the wireless receiver 30 detects a vital sign impedance waveform signal. In the embodiment, the electrocardiographic waveforms signal and the electrode detachment detection signal can be output to the output terminals R', F', and L' in the same manner as in the embodiment shown in FIGS. 5A and 5B. Like constituent elements are assigned like reference numerals, and their repeated explanations are omitted.

A vital sign impedance waveform signal is detected by electrodes G, H which act as second vital sign signal detection means. The thus-detected vital sign impedance waveform signal is synthesized with a 48-kHz signal supplied from a constant current source 71. The vital sign signal synthesized with the 48-kHz signal supplied from the constant current source 71 is input to the control circuit 67 flowing through amplifiers 72, an amplifier 74, a detector/half-wave rectifier 76, and a high pass filter 77. As in the case of the embodiment shown in FIGS. 5A and 5B, the vital sign impedance waveform signal can be reproduced while being superimposed on the electrocardiographic waveform signal through the control circuit 67, by a pseudo resistor serving as superimposing means 68 connected between the output terminal R' of the differential amplifier 66a and the output terminal L' of the differential amplifier 66b.

Figure 7:
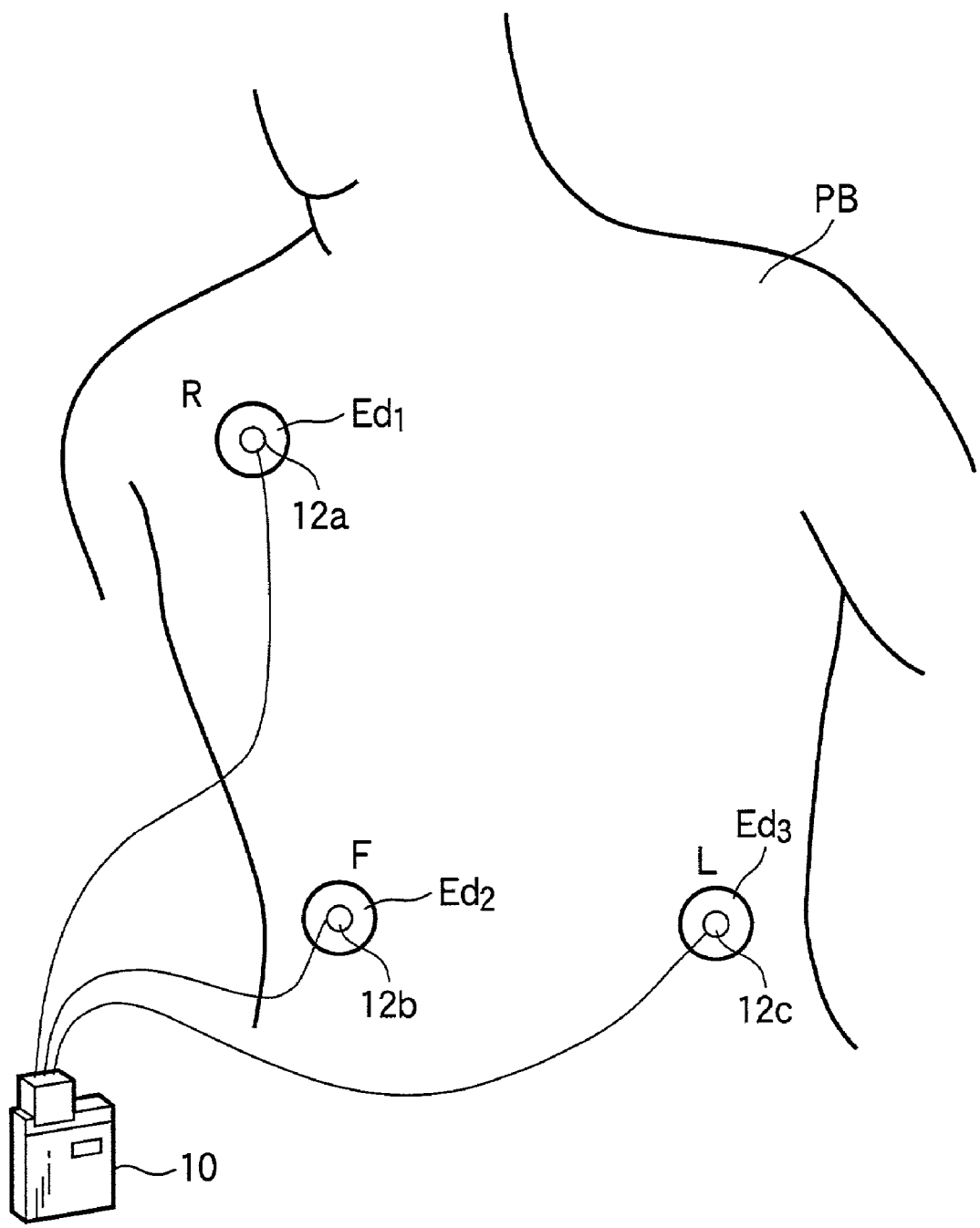
FIG. 7 is a descriptive view showing a wireless transmitter employed in the medical telemeter system according to the invention and an example in which electrodes of the system are attached to a patient.

FIG. 7 shows a wireless transmitter 10A constituting the medical telemetry system according to the invention (see FIG. 1) and an example in which the electrodes Ed1, Ed2, and Ed3 are attached to tissue surface. By the embodiment, the positions of the electrodes can be applied to those of electrodes using the wireless transmitter 10 shown in FIG. 3.

Figure 8:
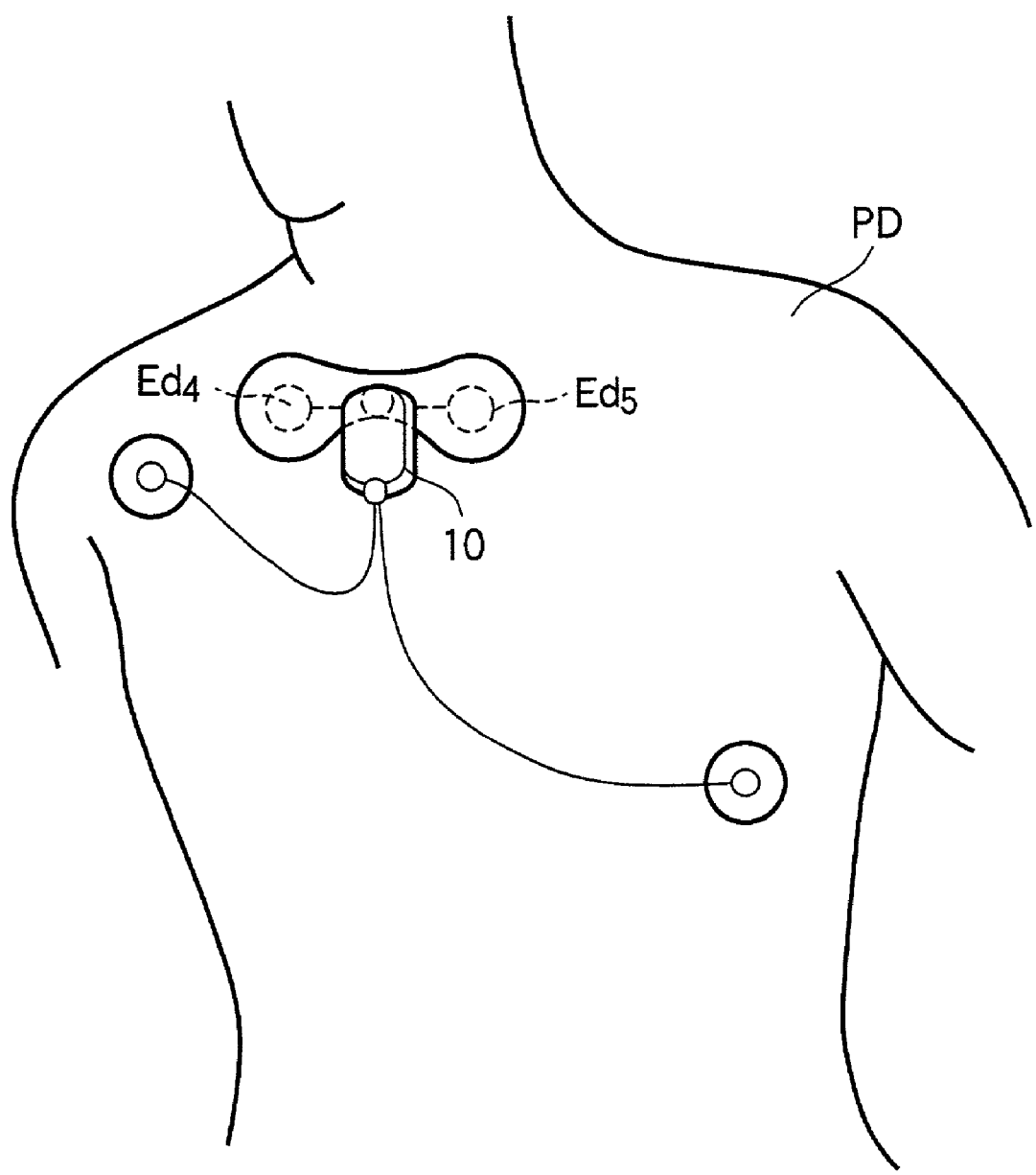
FIG. 8 is a descriptive view showing a wireless transmitter employed in the medical telemeter system according to the invention and another example in which electrodes of the system are attached to the patient.

FIG. 8 shows a wireless transmitter 10B constituting the medical telemetry system according to the invention (see FIG. 1) and an example in which the electrodes Ed4, Ed5 are attached to tissue surface. By the embodiment, the positions of the electrodes can be applied to those of electrodes of the wireless transmitter 10 shown in FIG. 4.

Figure 9:
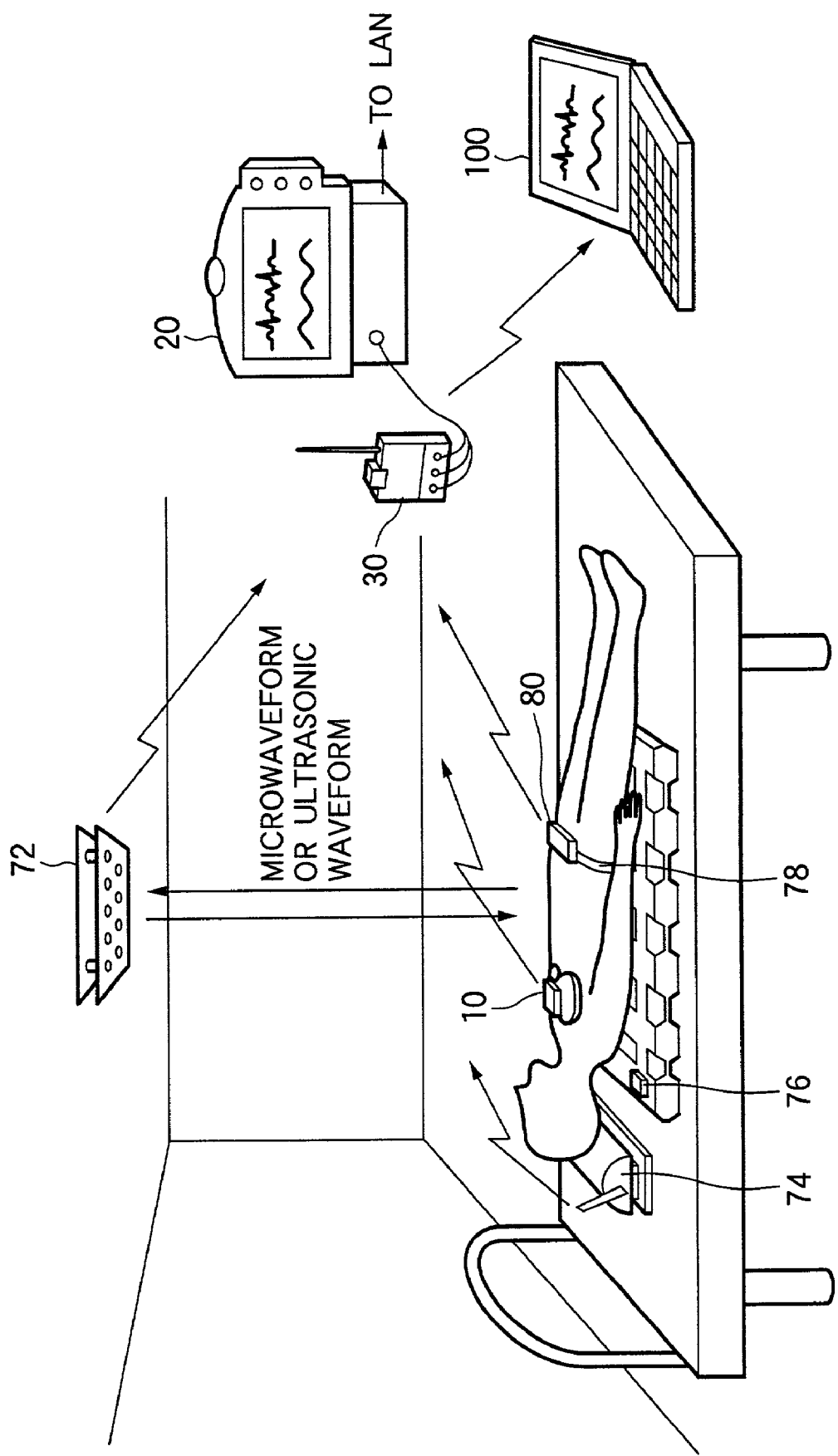
FIG. 9 is a descriptive view showing a second vital sign signal detection means used in the medical telemetry system according to the invention.

FIG. 9 shows means for detecting a second vital sign signal other than electrocardiographic waveform signal constituting the medical telemetry system according to the invention. The second vital sign signal detection means is constructed as a second vital sign signal sensor. The second vital sign signal sensor transmits, to the wireless transmitter 10, a second vital sign signal while being superimposed on an electrocardiographic signal. Alternatively, the second vital sign signal detection means can be constructed as second vital sign signal detection means 36 (see FIG. 1) provided in the wireless receiver 30.

The second vital signal detection means shown in FIG. 9 is arranged so as to detect a respiratory wave of the patient. Reference numeral 72 designates a sensor mounted on a ceiling. The sensor 72 radiates a microwave or ultrasonic wave onto the patient PD. A respiratory wave is detected by a displacement in phase difference between the radiated wave and a reflected wave. Reference numeral 74 designates a load sensor, such as a strain gauge, provided in a pillow on which the patient's head PD is situated. The sensor 74 is arranged to detect a respiratory wave by displacement of the head stemming from respiratory action of the patient PD. Reference numeral 76 designates a pneumatic sensor provided on an air mat laid below the patient PD. The sensor 76 is constructed to detect a respiratory wave, by variations in air pressure of an air mat which is subjected to fluctuations due to respiration of the patient PD. Reference numeral 78 designates an elastic belt around the waist of the patent PD, is equipped with a strain gauge or the like, and possesses elasticity. The belt 78 is constructed to detect a respiratory wave by variations in tensile strength of the belt elastic due to respiration of the patient PD. Reference numeral 80 designates a sensor which is provided in the waist of the patient PD and equipped with a coil for detecting variations in earth magnetism. The sensor 80 is arranged to detect a respiratory wave by detecting changes in earth magnetism through the coil which are due to respiration of the patient PD. A respiratory wave can be detected by any one of the devices. Here, the signal received by the wireless receiver 30 may be transmitted to a computer 100.

Figure 10:
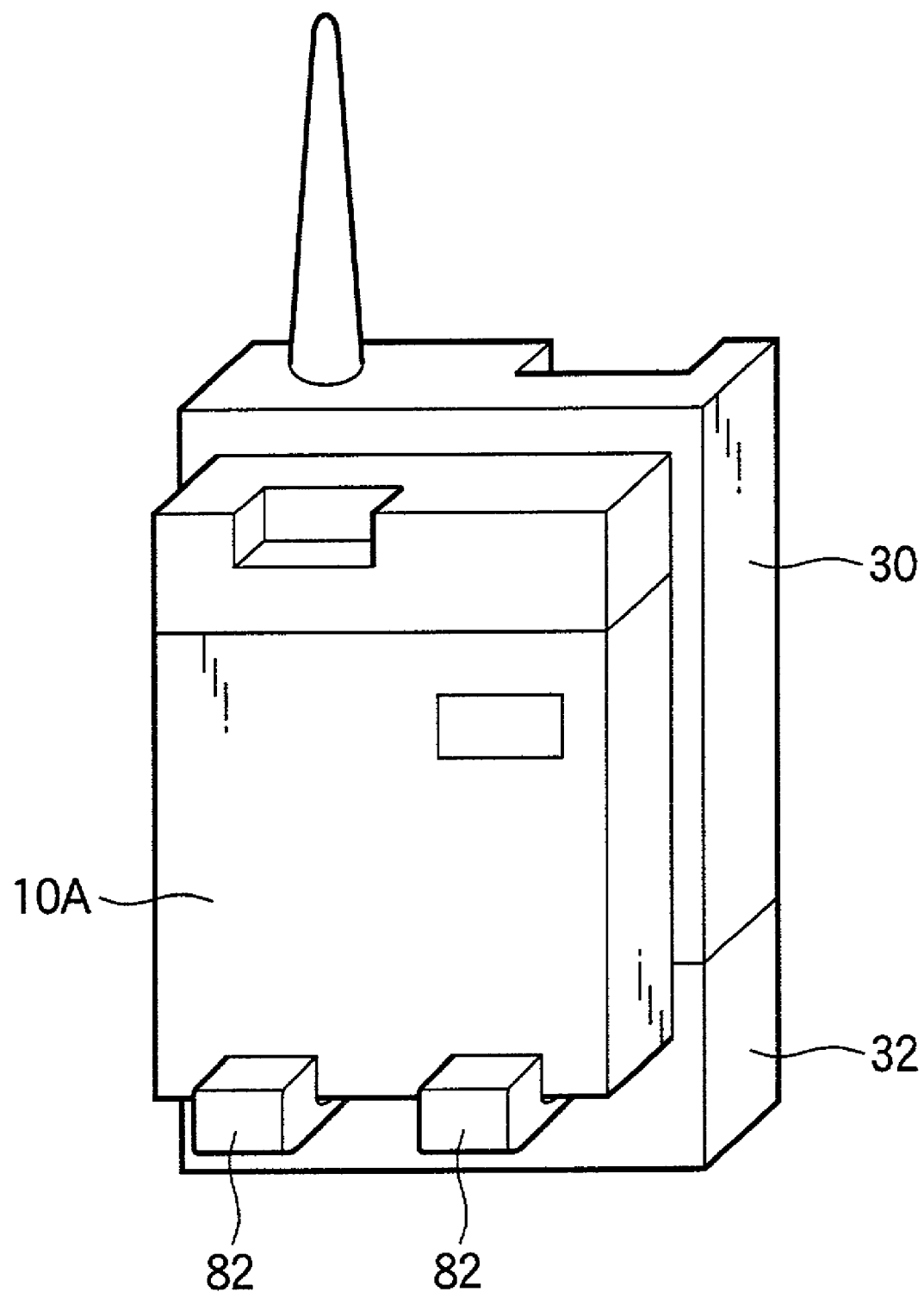
FIG. 10 is a descriptive view showing a wireless transmitter and a wireless receiver, which are employed in the medical telemetry system according to the invention, when they are attached together.

FIG. 10 shows a combination of the wireless receiver 30 and the wireless transmitter 10A, which constitute a medical telemetry system according to the invention. In the embodiment, the wireless receiver 30 is provided with engagement claws 82, 82, as required. The wireless transmitter 10 is detachably attached to the claws 82, 82. Such a construction enables immediate use of a medical telemetry system for an emergency medical aid in a medical institution.

Similarly, FIGS. 11A and 11B are for describing a structure which enables combination of the wireless receiver 30 and the wireless transmitter 10B. The wireless receiver 30 has a built-in antenna, and an opening 30a is formed in the receiver 30 so that the receiver 30 can be hooked on a pole for holding an infusion bag. A convex hook 30b to be engaged with a concave hook 10c is formed in the receiver 30, wherein the hook 10c is provided for connection with the adhesive pads 16 of the wireless transmitter 10B (see FIG. 11B) By such a construction, when not in use, the wireless transmitter 10B and the wireless receiver 30 can be fixed and stored together by the hooks (see FIG. 11A).

Preferred embodiments of the invention have been described thus far. The present invention is not limited to the embodiments and may be subjected to many design changes within the scope of the invention.

As is obvious from the foregoing embodiments, A medical telemetry system including:

a transmitter having a first detection section for detecting a first vital sign signal from a first sensor and a modulation circuit which modulates a signal detected by the first detection section to transmit the modulated signal by radio wave transmission;

a receiver having demodulation means which receives the detection signal that has been transmitted by radio wave transmission and demodulates the received signal and a connector for transmitting the demodulated signal output by the demodulation means to a vital sign signal input section of the vital sign signal monitor, wherein the connector of the receiver is connectable with a commonly used vital sign signal input section of each of various types of vital sign signal monitors. There is yielded an advantage of the ability to readily and conveniently utilize the vital sign signal monitor in the form of a wire system or a wireless system.

So long as the medical telemetry system according to the invention is set such that a second vital sign signal is detected by the first sensor or such that a second vital sign signal is detected by means other than the first sensor, the first vital sign signal and the second vital sign signal are multiplexed. The thus-multiplexed signal is transmitted from the transmitter to the receiver, thereby readily realizing a multifunctional medical telemetry system.

The medical telemetry system according to the invention is provided with a sensor detachment detection section for detecting detachment of the first sensor. The sensor detachment detection signal is multiplexed along with the first and second vital sign signals, and the thus-multiplexed signal is transmitted to the receiver from the transmitter. Here, the vital sign signal monitor can receive a normal vital sign signal at all times. There are yielded many advantages: for example, the advantage of being able to improve the reliability of the medical telemetry system.

Further, in an electric circuit for reproducing detachment of a sensor for detecting a vital sign signal, a switch for turning off it when the detachment of the sensor is occurred is provided on the signal line for transmitting a vital sign signal to reproduce the detachment of the switch by deactivation.

Moreover, it is preferable that the switch has a characteristic of leakage current flowing from the switch being lower than a predetermined current value when the power supplied from the power supply section has become consumed to prevent the vital sign signal monitor from erroneously recognizing that the leakage current is signal detected by the sensor.

What is claimed is:

1. A medical telemetry system, comprising:
   a first sensor, adapted to be attached on a living body to detect a first vital sign signal;
   a first transmitter, adapted to be connected to the first sensor and transmitting the first vital sign signal by radio wave transmission;
   a receiver, receiving the first vital sign signal transmitted from the first transmitter;
   a connector, integrally provided with the receiver and having a first terminal operable to output at least the first vital sign signal received by the receiver;
   at least one monitor, operable to display at least the first vital sign signal; and
   a connection wire, having a first end adapted to be connected to the monitor and a second end provided with a second terminal adapted to be detachably connected to the first sensor and to be detachably connected to the first terminal.

2. The medical telemetry system as set forth in claim 1, wherein the connector is detachably connected with the receiver.

3. The medical telemetry system as set forth in claim 1, wherein:
   the first sensor is operable to detect a second vital sign signal; and
   the first transmitter is operable to transmit the first vital sign signal and the second vital sign signal in a multiplexing manner.

4. The medical telemetry system as set forth in claim 3, wherein the receiver is operable to demultiplex the first vital sign signal and the second vital sign signal, and is operable to transmit the first vital sign signal and the second vital sign to the first terminal in a superimposing manner.

5. The medical telemetry system as set forth in claim 4, wherein the second vital sign signal is superimposed using an impedance change technique.

6. The medical telemetry system as set forth in claim 3, wherein the first vital sign signal is an electrocardiographic waveform of the living body, and the second vital sign signal is a respiratory status of the living body.

7. The medical telemetry system as set forth in claim 1, further comprising a second sensor, adapted to be attached on the living body to detect a second vital sign signal,
   wherein the first transmitter is operable to transmit the first vital sign signal and the second vital sign signal in a multiplexing manner.

8. The medical telemetry system as set forth in claim 7, wherein the first vital sign signal is an electrocardiographic waveform of the living body, and the second vital sign signal is a respiratory status of the living body.

9. The medical telemetry system as set forth in claim 7, wherein the receiver is operable to demultiplex the first vital sign signal and the second vital sign signal, and is operable to transmit the first vital sign signal and the second vital sign signal to the first terminal in a superimposing manner.

10. The medical telemetry system as set forth in claim 9, wherein the second vital sign signal is superimposed using an impedance change technique.

11. The medical telemetry system as set forth in claim 1, further comprising:
   a second sensor, adapted to be attached on the living body to detect a second vital sign signal; and
   a second transmitter, adapted to be connected to the second sensor and transmitting the second vital sign signal by radio wave transmission, wherein:
   the receiver is operable to receive the second vital sign signal transmitted from the second transmitter and to transmit the first vital sign signal and the second vital signal to the first terminal in a superimposing manner; and
   the second terminal of the connection wire is further adapted to be detachably connected to the second sensor.

12. The medical telemetry system as set forth in claim 11, wherein the second vital sign signal is superimposed using an impedance change technique.

13. The medical telemetry system as set forth in claim 11, wherein the first vital sign signal is an electrocardiographic waveform of the living body, and the second vital sign signal is a respiratory status of the living body.

14. The medical telemetry system as set forth in claim 11, wherein the second terminal is provided with at least one of a hook member and a clip member.

15. The medical telemetry system as set forth in claim 1, further comprising a switch operable to cut off the output of the at least first vital sign signal from the first terminal, wherein:
   the transmitter is operable to detect detachment of the first sensor from the living body; and
   the switch cuts off the output of the at least first vital sign signal when the transmitter detects the detachment of the first sensor.

16. The medical telemetry system as set forth in claim 1, wherein the second terminal is provided with at least one of a hook member and a clip member.

* * * * *